(12) United States Patent
Mahavadi et al.

(10) Patent No.: US 11,550,975 B2
(45) Date of Patent: Jan. 10, 2023

(54) METHODS AND SYSTEMS FOR PREDICTING INTERFACIAL TENSION OF RESERVOIR FLUIDS USING DOWNHOLE FLUID MEASUREMENTS

(71) Applicants: Schlumberger Technology Corporation, Sugar Land, TX (US); Saudi Arabian Oil Company, Dhahran (SA)

(72) Inventors: Sharath Chandra Mahavadi, Lexington, MA (US); Robin Singh, Oakmont, PA (US); Wael Abdallah, Al-Khobar (SA); Mohammed Al-Hamad, Saihat (SA); Bastian Sauerer, Khobar (SA); Shouxiang Ma, Dhahran (SA); Leilei Zhang, Houston, TX (US)

(73) Assignees: SCHLUMBERGER TECHNOLOGY CORPORATION, Sugar Land, TX (US); SAUDI ARABIAN OIL COMPANY, Dhahran (SA)

(*) Notice: Subject to any disclaimer, the term of this patent is extended or adjusted under 35 U.S.C. 154(b) by 84 days.

(21) Appl. No.: 16/940,436

(22) Filed: Jul. 28, 2020

(65) Prior Publication Data
US 2022/0035971 A1 Feb. 3, 2022

(51) Int. Cl.
*G01N 33/28* (2006.01)
*E21B 49/08* (2006.01)
(Continued)

(52) U.S. Cl.
CPC .............. *G06F 30/27* (2020.01); *E21B 47/07* (2020.05); *E21B 49/081* (2013.01);
(Continued)

(58) Field of Classification Search
CPC .............. E21B 49/081; E21B 49/0813; E21B 49/0815; E21B 49/0875; E21B 49/087;
(Continued)

(56) References Cited

U.S. PATENT DOCUMENTS

| | | | | |
|---|---|---|---|---|
| 8,589,130 | B2 * | 11/2013 | Stukan | G16C 20/30 73/64.55 |
| 2015/0275648 | A1 * | 10/2015 | Wang | E21B 44/00 702/9 |

(Continued)

FOREIGN PATENT DOCUMENTS

WO 2016018229 A1 2/2016

OTHER PUBLICATIONS

Andersen, S. I. et al, "Detection and Impact of Carboxylic Acids at the Crude Oil-Water Interface", Energy Fuels, 2016, 30, pp. 4475-4485.
(Continued)

*Primary Examiner* — Catherine Loikith

(57) ABSTRACT

Methods and systems are provided for characterizing interfacial tension (IFT) of reservoir fluids, which involves obtaining fluid property data that represents fluid properties of a reservoir fluid sample measured downhole at reservoir conditions, and inputting the fluid property data to a computational model that determines a value of oil-water IFT of the reservoir fluid sample based on the fluid property data. In embodiments, the fluid property data represents single-phase fluid properties of the reservoir fluid sample, such as fluid density and viscosity of an oil phase of the reservoir fluid sample and fluid density of a water phase of the reservoir fluid sample. In embodiments, the computation model can be based on machine learning or analytics combined with a thermodynamics-based physics model.

26 Claims, 6 Drawing Sheets

(51) Int. Cl.
G06F 30/27 (2020.01)
G01N 11/00 (2006.01)
G01N 9/00 (2006.01)
G01V 99/00 (2009.01)
E21B 47/07 (2012.01)
G06F 111/10 (2020.01)
E21B 41/02 (2006.01)
E21B 49/10 (2006.01)
E21B 43/38 (2006.01)

(52) U.S. Cl.
CPC .......... *E21B 49/0875* (2020.05); *G01N 9/00* (2013.01); *G01N 11/00* (2013.01); *G01N 33/2823* (2013.01); *G01V 99/005* (2013.01); *E21B 41/02* (2013.01); *E21B 43/38* (2013.01); *E21B 49/087* (2013.01); *E21B 49/10* (2013.01); *E21B 2200/20* (2020.05); *G06F 2111/10* (2020.01)

(58) Field of Classification Search
CPC .. E21B 2200/20; E21B 33/00; G01N 33/2823
See application file for complete search history.

(56) References Cited

U.S. PATENT DOCUMENTS

2018/0119534 A1* 5/2018 Jamison ............... G05B 17/00
2020/0096429 A1  3/2020 Andersen et al.

OTHER PUBLICATIONS

Firoozabadi, A. et al., "Surface Tension of Water-Hydrocarbon Systems at Reservoir Conditions," Journal of Canadian Petroleum Technology, 1988, 27(3), pp. 41-48.

Jamialahmadi, M. et al., "Generalized set of correlations for plus fraction characterization," Petroleum Science, 2012, 9(3), pp. 370-378.

Ling, K. et al., "A New Correlation to Calculate Oil-Water Interfacial Tension", SPE 163328, presented at the SPE Kuwait International Petroleum Conference and Exhibition held in Kuwait City, Kuwait, 2012, 9 pages.

Melrose, J.C. et al, "Role of Capillary Forces in Determining Microscopic Displacement Efficiency for Oil Recovery by Waterflooding", The Journal of Canadian Petroleum, PETSOC-74-04-05-P, 1974, 13(4), 9 pages.

Sauerer, B. et al., "Dynamic Asphaltene-Stearic Acid Competition at the Oil-Water Interface", Langmuir, 2018, 34, pp. 5558-5573.

Sutton, R. P., "An Improved Model for Water-Hydrocarbon Surface Tension at Reservoir Conditions", SPE 124968, presented at the 2009 Annual Technical Conference and Exhibition, New Orleans, Louisiana, USA, pp. 1-18.

Zuo, Y.-X. et al, "Prediction of Interfacial Tension of Reservoir Crude Oil and Gas Condensate Systems," SPE 38434, SPE Journal, 1998, pp. 134-145.

Kesler, M. G. et al, "Improve Prediction of Enthalpy of Fractions," Hydrocarbon Processing, 1976, 55(3), pp. 153-158.

Riazi, M. R. et al., "Simplify Property Predictions", Hydrocarbon Processing, Gulf Publishing U.S.A., 1980, 59(3), pp. 115-116.

Riazi, M. R. et al., "Characterization Parameters for Petroleum Fractions", Industrial & Engineering Chemistry Research, 1987, 26(4), pp. 755-759.

* cited by examiner

METHODS AND SYSTEMS FOR PREDICTING INTERFACIAL TENSION OF RESERVOIR FLUIDS USING DOWNHOLE FLUID MEASUREMENTS

FIELD

The present disclosure relates to characterizing properties of petroleum reservoir fluids, and, more particularly, to determining interfacial tension (IFT) between the hydrocarbons, especially oil phase, and water phase of such petroleum reservoir fluids.

BACKGROUND

Petroleum reservoir fluids can include a hydrocarbon (gas and/or crude oil) phase and water phase (i.e., brine or formation water). Knowledge of the interfacial tension (IFT) between the hydrocarbon phase and water phase of petroleum reservoir fluids can play an important role in the evaluation of reservoir potential and its performance. It is also an important property for dynamic reservoir performance simulation. For liquid hydrocarbons, the oil phase can have different types of surface-active components including naphthenic acids. Naphthenic acids play an important role in controlling the IFT between the oil phase and the water phase in reservoir fluids, but IFT is dominated by the bulk properties of the immiscible fluids, i.e., density and viscosity and the environmental conditions such as temperature.

IFT is an important property between fluids controlling distribution and flow of a fluid of oil and water in porous media, as capillary pressure $P_c$ is linearly dependent on it. If the porous medium is modeled by the cylindrical tube model, fluid distribution at equilibrium is controlled by the capillary pressure $P_c$, written as:

$$P_c = \frac{2\gamma_{ow}\cos\theta}{r} \qquad \text{Eqn. (1)}$$

where $P_c$ is capillary pressure, $\gamma_{ow}$ is the IFT between the oil phase and the water phase of the fluid, $\theta$ is the wetting angle, and r is the pore throat radius.

Since the capillary pressure $P_c$ determines fluid distribution at equilibrium, one application of IFT is in oil reserve calculations such as saturation height function modeling. The height of the hydrocarbon column is calculated by equating the capillary pressure (Eqn. 1) with buoyancy pressure, $\Delta\rho\mu gH$ resulting in:

$$H = \frac{2\gamma_{ow}\cos\theta}{rg(\rho_w - \rho_o)} \qquad \text{Eqn. (2)}$$

where H is the hydrocarbon column height above free water level, g is gravity constant, and $\rho_w$ and $\rho_o$ are densities of the water phase and oil phase, respectively.

Fluid flow in the porous media can be determined by the balance between the capillary pressure $P_c$ and a driving force. The driving force can be a displacing viscous force that defines the capillary number $N_c$, or gravity that the bond number can be estimated. The capillary number $N_c$ is defined as the ratio between viscous and capillary forces. There are many forms of expressions for capillary number $N_c$ expressions, such as the following from Melrose, J. C., Brandner, C. F., 1974 "Role of capillary forces in determining microscopic displacement efficiency for oil recovery by waterflooding," The Journal of Canadian Petroleum, PETSOC-74-04-05-P:

$$N_c = \frac{\mu_w V_w}{\vartheta} \frac{1}{\gamma_{ow}} \qquad \text{Eqn. (3)}$$

where Nc is the capillary number, $\mu_w$ is the viscosity of aqueous or displacing phase, $V_w$ is the flow rate of the displacing phase and $\vartheta$ is the effective porosity of formation.

From these equations, it is evident that the capillary pressure $P_c$ thus IFT (Eqn. 1) plays an important role in determining initial water saturation (Eqn. 2), residual oil saturation and oil displacement efficiency, i.e., oil recovery (Eqn. 3).

Variations or deviations from actual magnitudes in the order of up to 30% of the estimated IFT can have significant impact on reservoir evaluations (both reserves and recoveries) and therefore on asset economics.

In currently used models, such as those models described in i) Sutton, R. P., 2009 "An Improved Model for Water-Hydrocarbon Surface Tension at Reservoir Conditions," SPE Annual Technical Conference and Exhibition, SPE 124968, 1-18; ii) Ling, K.; He, J., 2012 "A New Correlation to Calculate Oil-Water Interfacial Tension," SPE-163328, SPE Kuwait International Petroleum Conference and Exhibition; iii) Firoozabadi, A.; Ramey, H. J., 1988 "Surface tension of water-hydrocarbon systems at reservoir conditions," J. Can. Pet. Technol. 27, 41-48; and iv) Zuo, Y.-X.; Stenby, E. H., 1998 "Prediction of Interfacial Tensions of Reservoir Crude Oil and Gas Condensate Systems," SPE Journal 3(2), 134-145, the value of IFT can be overestimated, which can result in high uncertainties in evaluating reserves and recoveries by up to 25%. See Li, H.; Mahavadi, S. C.; Andersen, S. I., 2014 "Method and apparatus for the analysis of Reservoir Fluids," WO/2016/018229.

Reservoir engineers commonly estimate the IFT between the oil phase and water phase of reservoir fluids and its variation over a reservoir based solely on the hydrocarbon composition of the reservoir fluids reported from standard gas chromatographic analysis given in PVT reports. Crude oils contain thousands of components. Among them, surface-active species, such as carboxylic acids, are of special interest, as they dominate the properties of the oil/water interface. Even in small quantities, they can have a significant effect on the interfacial properties as described in Sauerer, B.; Stukan, M.; Buiting, J.; Abdallah, W.; Andersen, S., 2018 "Dynamic Asphaltene-Stearic Acid Competition at the Oil-Water Interface", Langmuir 34, 5558-5573 and Andersen, S. I.; Mahavadi, S. C.; Chen, J.; Zeng, B. Y.; Zou, F.; Mapolelo, M.; Abdallah, W.; Buiting, J. J., 2016 "Detection and Impact of carboxylic acids at the crude oil-water interface," Energy & Fuels 30 (6), 4475. Thus, the applied correlations, lacking a surface-active component term, are not suitable for crude oil IFT estimation.

To account for the active-species contribution to IFT, US Patent Publ. No. US20200096429A1 to Andersen et al., 2016, describes a method that employs a downhole tool for fluid sampling, analysis, and calculation of IFT based on acid-base IFT contribution. In this method, concentrations of surface-active species are measured using a spectrometer. In PCT Patent Publ. No. WO2016018229A1 to Li et al., 2014, a method is proposed that samples a reservoir fluid and applies an empirical model that relates oil-water IFT of the sample to concentration of at least one organic acid species. This model requires calibration based on the measured oil-water interfacial tension of the sample.

It is, however, a challenging task to estimate the concentration of these surface-active components in the crude oil, especially in downhole estimations, making it challenging to correct for their influence. When crude oil and kerogen mature under temperature and pressure, the in-situ composition changes through cracking and biodegradation, leading to the creation and decomposition of different organic species. In this process, the crude oil viscosity and density, as well as the concentration of surface-active species will undergo changes.

In reservoir modeling, the current approach for IFT estimation is the so-called Sutton equation, which has been implemented in software (e.g. PIPESIM, a Schlumberger software) to characterize multiphase flow of reservoir fluids. The Sutton equation has the form:

$$\gamma_{ow} = \left[\frac{1.58(\rho_w - \rho_o) + 1.76}{T_r^{0.3125}}\right]^4 \quad \text{Eqn. (4)}$$

where $\gamma_{ow}$ is the IFT between the oil phase and the water phase of the reservoir fluid, $\rho_w$, and $\rho_o$ are density of the water phase and oil phase, respectively, and $T_r$ is reduced temperature or ratio of the critical temperature ($T_c$) of the oil phase and the temperature (T) of the system.

The critical temperature ($T_c$) of the oil phase is that temperature above which the oil phase cannot exist as a liquid, no matter how much pressure is applied, a very difficult parameter to obtain even in the laboratory conditions. Note that the Sutton equation is described in Sutton, R. P., 2009 "An Improved Model for Water-Hydrocarbon Surface Tension at Reservoir Conditions," SPE Annual Technical Conference and Exhibition, SPE 124968, 1-18.

Several other correlations exist (e.g., based on Parachor number), but an approach where the impact of crude oil components is properly accounted for is currently lacking.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In accordance with the subject disclosure, methods and systems are provided for characterizing interfacial tension (IFT) of reservoir fluids, which involves obtaining fluid property data that represents fluid properties of a reservoir fluid sample measured downhole at reservoir conditions, and inputting the fluid property data to a computational model that determines a value of oil-water IFT of the reservoir fluid sample based on the fluid property data.

In embodiments, the fluid property data represents single-phase fluid properties of the reservoir fluid sample, such as fluid density and viscosity of an oil phase of the reservoir fluid sample and fluid density of a water phase of the reservoir fluid sample.

In embodiments, the computational model can be configured to relate critical temperature of an oil phase of the reservoir fluid sample to oil-water IFT of the reservoir fluid sample. The computation model can also be configured to relate single-phase fluid properties (such as fluid density and viscosity) of the oil phase of the reservoir fluid sample to the critical temperature of the oil phase of the reservoir fluid sample.

In embodiments, the computational model can have the form $$\gamma_{OW} = \left[\frac{1.58(\rho_w - \rho_o) + 1.76}{\left(\frac{T}{G(\mu, \rho_0)}\right)^{0.3125}}\right]^4,$$

where $\gamma_{ow}$ is the value of the oil-water IFT of the reservoir fluid sample, $\rho_w$ and $\rho_o$ are density of a water phase and oil phase, respectively, T is the reservoir temperature as part of the reservoir conditions, and $G(\mu, \beta_0)$ represents critical temperature of the oil phase given the fluid density $\rho_0$ and viscosity $\mu$ of the oil phase.

In embodiments, the methods and systems can further involve storing the value of the oil-water IFT of the reservoir fluid sample in a database and/or storing the value of the oil-water IFT of the reservoir fluid sample as part of data accessible by an advisory tool for reservoir analysis and optimization.

In embodiments, all or part of the operations of the methods or systems can be performed by a processor.

BRIEF DESCRIPTION OF THE DRAWINGS

The subject disclosure is further described in the detailed description which follows, in reference to the noted plurality of drawings by way of non-limiting examples of the subject disclosure, in which like reference numerals represent similar parts throughout the several views of the drawings, and wherein.

DETAILED DESCRIPTION

The particulars shown herein are by way of example and for purposes of illustrative discussion of the embodiments of the subject disclosure only and are presented in the cause of providing what is believed to be the most useful and readily understood description of the principles and conceptual aspects of the subject disclosure. In this regard, no attempt is made to show structural details in more detail than is necessary for the fundamental understanding of the subject disclosure, the description taken with the drawings making apparent to those skilled in the art how the several forms of the subject disclosure may be embodied in practice. Furthermore, like reference numbers and designations in the various drawings indicate like elements.

The physical fluid properties of crude oil such as critical temperature, critical pressure, boiling point are governed by two key elements, intermolecular forces and the molecular size of the respective hydrocarbon molecules. Any physical property of the crude oil, such as the critical temperature ($T_a$), can be expressed in terms of two other properties of crude oil characterizing the two elements. For example, $$T_c = a\varphi_1^b \varphi_2^c \qquad \text{Eqn. (5)}$$

where ($\varphi_1$, $\varphi_2$) could be a pair of two properties such as temperature and specific gravity (T, SG), boiling point and refractive index ($T_b$, I), molecular weight and specific gravity (M, SG), molecular weight and refractive index (M, I), molecular weight and carbon-to-hydrogen weight ratio (M, CH), kinematic viscosity at 38° C. and specific gravity ($v_{38}$, SG), etc.

In these examples, $T_b$ is the boiling point, SG is the specific gravity, M is the molecular weight, I is the refractive index, CH is the carbon-to-hydrogen weight ratio, and $v_{38}$ is kinematic viscosity at 38° C.

The detailed exponents of such correlations are available in the literature, such as Riazi, M. R.; Daubert, T. E., 1980 "Simplify property predictions," Hydrocarbon Proc. 59, 115-116. Three examples of correlations that predict critical temperature $T_c$ are given in the following:

$$a)\varnothing = a[\exp^{(b\varnothing_1 + b\varnothing_2 + d\varnothing_1 \varnothing_2)}]\varnothing_1^e \varnothing_2^f \qquad \text{Eqn. (6)}$$

which is taken from Riazi, M. R.; Daubert, T. E., 1987 "Characterization Parameters for Petroleum Fractions. Ind. Eng. Chem. Res. 26 (4), 755-759;

$$b)\ T_c(K) = 189.8 + 450.6S + (0.4244 + 0.1174S)T_b + \frac{(0.1441 - 1.0069S)*10^5}{T_b} \qquad \text{Eqn. (7)}$$

which is taken from Kesler, M. G.; Lee, B. I., 1976 "Improve Prediction of Enthalpy of Fractions," Hydrocarbon Proc. 55 (3), 153-158; and $$c)\ T_c(K) = 239.4\ \ln(M) - 555.3 \qquad \text{Eqn. (8)}$$

which is taken from Jamialahmadi, M.; Zangeneh, H.; Hosseini, S. S. A., 2012 "Generalized Set of Correlations for plus Fraction Characterization," Pet. Sci. 9 (3), 370-378.

Figure 1A:
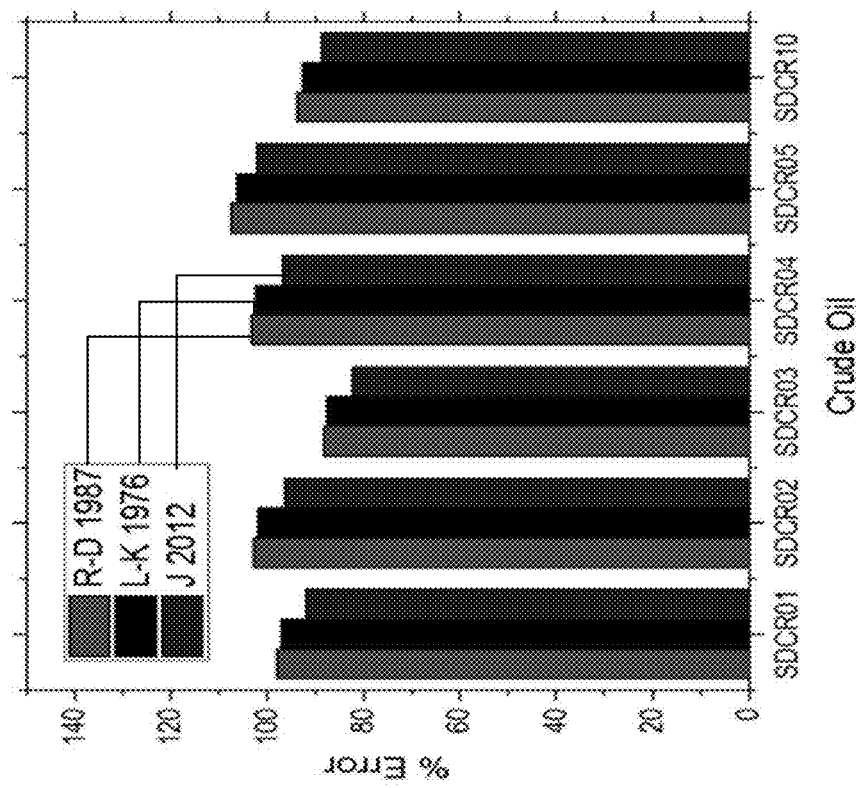
FIG. 1A depicts plots of critical temperature ($T_c$, in degrees Kelvin) of six crude oils using three correlations (labelled "R-D 1987," "L-K 1976," and "J 2012") and from measured IFT based on the Sutton model of Eqn. (4)
Figure 1B:
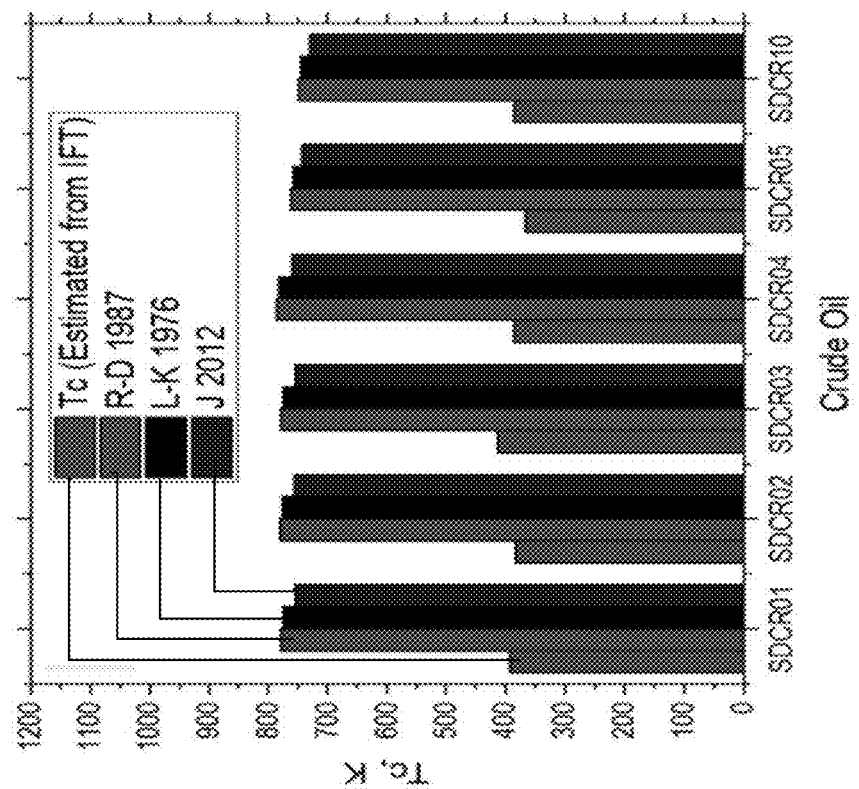
FIG. 1B depicts plots of variations in the critical temperature ($T_c$, in degrees Kelvin) of the six crude oils determined from the three correlations of FIG. 1A relative to the measured IFT based on the Sutton model of Eqn. (4) as shown in FIG. 1A.

FIG. 1A shows the prediction of critical temperature ($T_c$) for six crude oils, using three correlations of Eqn. (6) (labelled "R-D 1987"), Eqn. (7) (labelled "L-K 1976"), and Eqn. (8) (labelled "J 2012"). FIG. 1A also shows the values of critical temperature ($T_c$) for the six crude oils obtained using experimental data of IFT for the same oils and the Sutton model of Eqn. (4). FIG. 1B shows the deviations of the critical temperature ($T_c$) predicted by the three correlations relative to critical temperature ($T_c$) based on experimental data of IFT for the six crude oils. It is evident from the plots of FIG. 1A that the predictions from all three correlations were quite similar, but the deviations from the estimated $T_c$ based on experimental results (FIG. 1b) were very high with average errors of 99.1, 98.1 and 93.2% corresponding to R-D 1987, L-K 1976 and J 2012, respectively.

Figure 2B:
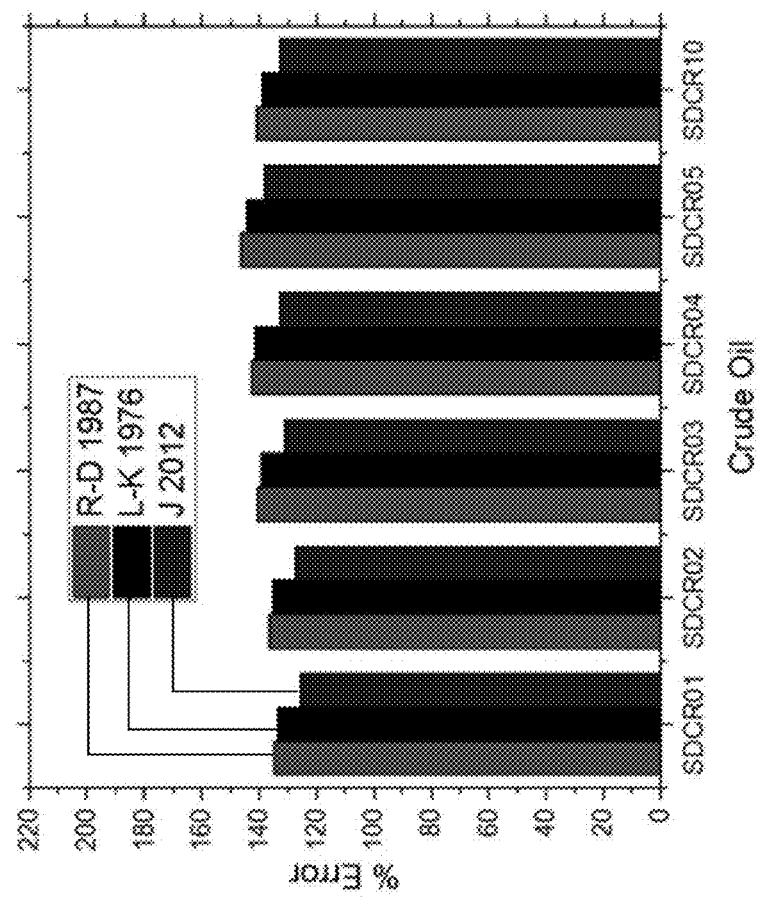
FIG. 2B depicts plots of variation in the oil-water IFT (in mN/m) for the six crude oils determined from the critical temperatures provided by the three correlations of FIG. 2A and the Sutton model of Eqn. (4) relative to the experimental oil-water IFT as shown in FIG. 2A.
Figure 2A:
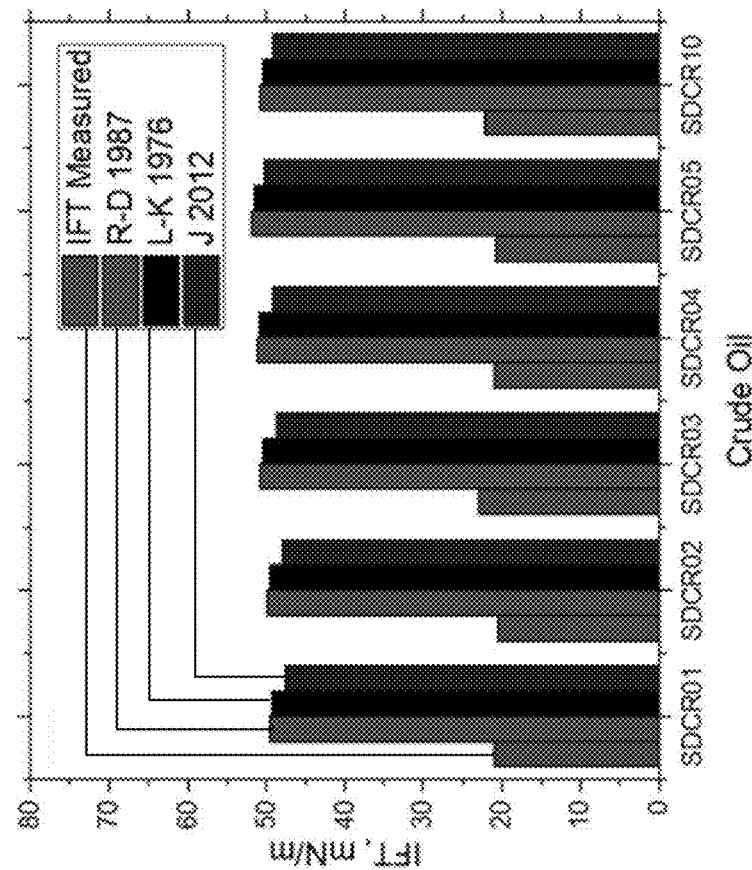
FIG. 2A depicts plots of oil-water IFT (in mN/m) for the six crude oils of FIGS. 1A and 1B determined from the critical temperatures provided by the three correlations of FIG. 1A and the Sutton model of Eqn. (4) and from experimental measurements.

Applying the prediction values of critical temperature ($T_c$) that result from these three correlations to the Sutton model of Eqn. (4) to predict IFT for the six crude oil samples produces results shown in the plots of FIG. 2A. As expected, there are high deviations in the predicted IFT values for the six crude oils relative to the measured experimental value as shown in the plots of FIG. 2B. Specifically, the plots of FIG. 2B show the average errors for the predicted IFT values based on the $T_c$ correlations, are 140.5, 139.0, 131.6% corresponding to R-D 1987, L-K 1976 and J 2012, respectively. Such errors are due to propagation of the errors in the predicted critical temperatures based on three $T_c$ correlations into the prediction of IFT.

In accordance with the present disclosure, a new physics-based computational model has been developed that uses fluid properties of a reservoir fluid sample measured downhole at reservoir conditions (temperature and pressure of the reservoir) to predict oil-water IFT of the reservoir fluid sample. In embodiments, the computational model can relate critical temperature of an oil phase of the reservoir fluid sample to oil-water IFT of the reservoir fluid sample. The computational model can also relate single-phase fluid properties of the reservoir fluid sample to the critical temperature of the oil phase of the reservoir fluid sample. In one embodiment, the computational model uses downhole measurements of fluid density and viscosity of the oil phase of a reservoir fluid sample at reservoir conditions (temperature and pressure) to predict oil-water IFT of the reservoir fluid sample.

In embodiments, the computation model can express the critical temperature $T_c$ of the oil phase of a reservoir fluid sample as a function of fluid density and viscosity of the oil phase as follows:

$$T_c = \frac{C}{[C' - F(\mu, \rho_0)]} * F(\mu, \rho_0) = G(\mu, \rho_0) \qquad \text{Eqn. (9)}$$

where $F(\mu, \rho_0)$ is a function or expression involving fluid density $\rho_0$ and viscosity $\mu$ of the oil phase at reservoir conditions (temperature and pressure) which can be inferred by downhole measurements, C and C' are constants, and the equivalent function $G(\mu, \rho_0)$ is also a function or expression involving fluid density $\rho_0$ and viscosity $\mu$ of the oil phase at reservoir conditions (temperature and pressure). Note that C and C' can be specific to the system under investigation and obtained from electronic memory as needed and combined with the fluid properties measured downhole. The parameters for Eqn. (9) can be obtained from linear and/or non-linear regression of a set of samples with known IFT and critical temperature $T_c$ of the oil phase of the samples calculated from the Sutton equation (4).

The model of Eqn. (9) can be combined with the Sutton model of Eqn. (4) to obtain the following Sutton-SLB-Aramco (SSA) computational model:

$$\gamma_{OW} = \left[ \frac{1.58(\rho_w - \rho_o) + 1.76}{\left(\frac{T}{G(\mu, \rho_0)}\right)^{0.3125}} \right]^4 \quad \text{Eqn. (10)}$$

where $\gamma_{OW}$ is the oil-water IFT of the reservoir fluid (which characterizes the interfacial tension between the oil phase and the water phase of the reservoir fluid), $\rho_w$ and $\rho_0$ are density of the water phase and oil phase, respectively, T is the temperature of the reservoir fluid as part of the reservoir conditions, and G ($\mu$, $\rho_0$) represents the critical temperature $T_c$ of the oil phase given the fluid density $\rho_0$ and viscosity $\mu$ of the oil phase. $G(\mu, \rho_0)$ may be reservoir fluid specific and can be fine-tuned. Note that the required input parameters of Eqn. (10) are fluid density and viscosity of the oil phase of the reservoir fluid.

In embodiments, the computational model can relate single phase fluid properties of the reservoir fluid measured at reservoir conditions (e.g., density $\rho_o$ and viscosity $\mu$ of the oil phase of the fluid, and density $\rho_w$ of the water phase of the reservoir fluid) as well as other fluid properties of the reservoir fluid (e.g., temperature T of the reservoir fluid as part of the reservoir conditions) to oil-water IFT of the reservoir fluid. The computational model can be based on machine learning or based on data analytics combined with a thermodynamics and physics-based model. For example, the computational model can employ an artificial neural network or system of artificial neural networks or other machine learning system. The machine learning system can be trained using supervised learning with reservoir fluid samples of known or labeled oil-water IFT. Alternatively, or additionally, the machine learning system can be trained in an unsupervised manner. In such systems, the computation model outputs a value of oil-water IFT of a reservoir fluid, given single phase fluid properties of the reservoir fluid measured at reservoir conditions as well as other fluid properties of the reservoir fluid as inputs. The computational model can provide data for evaluating and understanding reservoir connectivity (e.g., as part of the advisory tool 119 of FIG. 4 as described herein) and help with field development planning and production strategies, including suggestions and solutions for various challenges in a desired reservoir.

Figure 3:
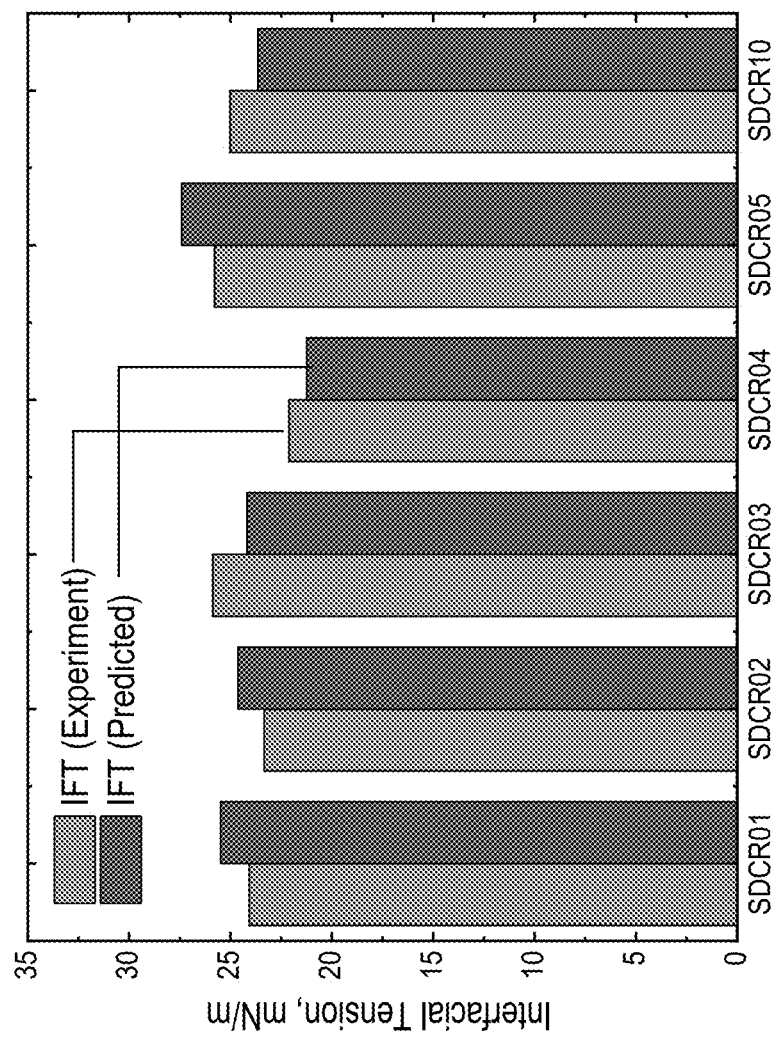
FIG. 3 depicts plots of oil-water IFT (in mN/m) for six crude oils determined from the Sutton-SLB-Aramco model of Eqn. (10) and from experimental measurements of oil-water IFT.

FIG. 3 shows the comparison between experimental values of oil-water IFT of the reservoir fluid sample IFT and predicted values of oil-water IFT of the reservoir fluid sample IFT using the SSA model of Eqn. (10). Note that the deviation between the experimental and the predicted values of IFT is reduced to within 6.5%.

Figure 4:
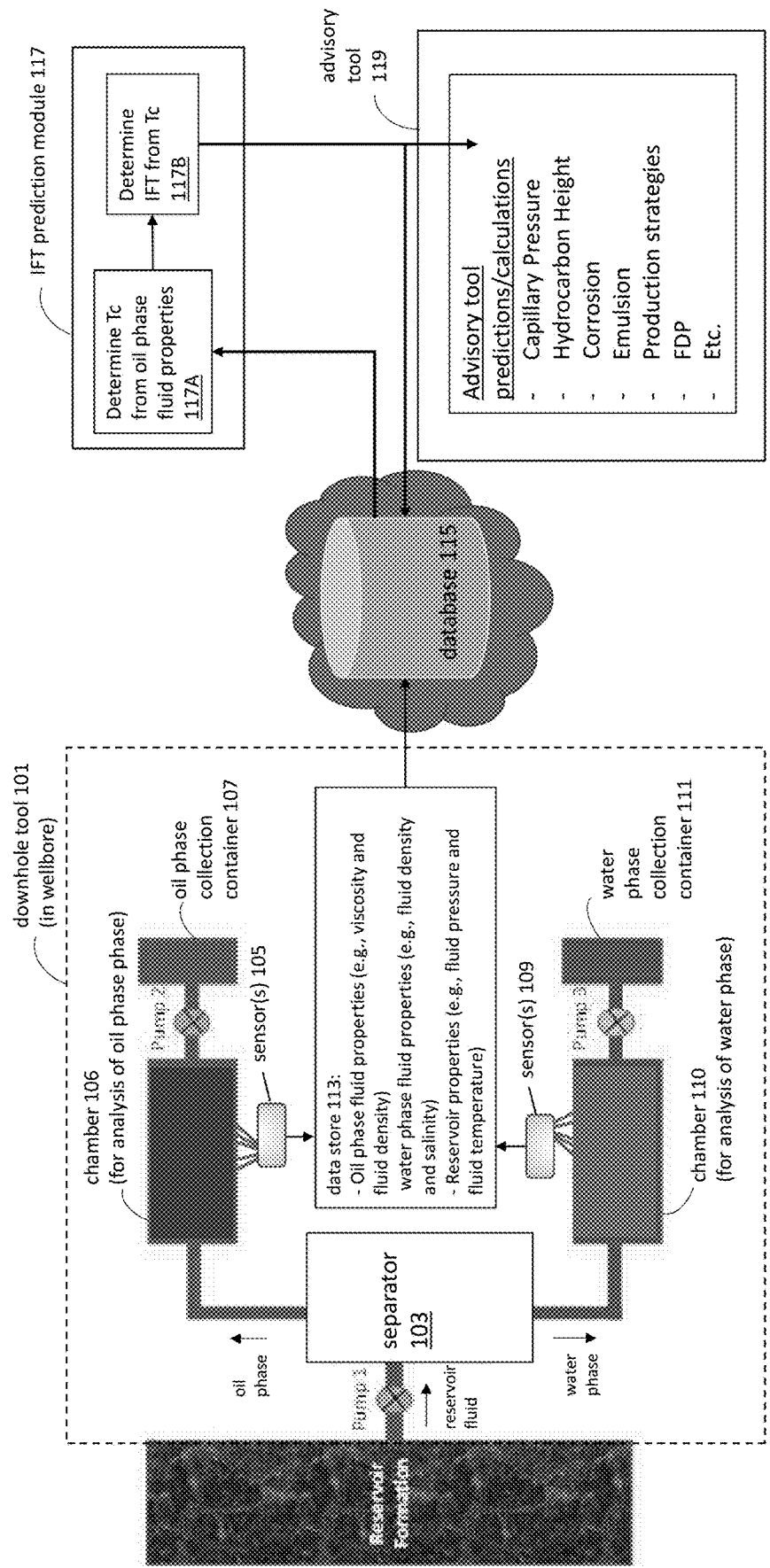
FIG. 4 is a schematic diagram illustrating a methodology and system for predicting oil-water IFT of a reservoir fluid sample using downhole measurements of fluid properties at reservoir conditions (temperature and pressure)

FIG. 4 shows a methodology and system for predicting oil-water IFT of the reservoir fluid sample using downhole measurements of fluid properties at reservoir conditions (temperature and pressure). During operation of a downhole tool 101 (for example, as described below with respect to FIG. 5), the tool 101 is positioned in the wellbore adjacent the reservoir formation and pump 1 is operated to draw in and collect a sample of the reservoir fluid from the reservoir formation under high temperature and high pressure reservoir conditions. The sample of the reservoir fluid under high temperature and high-pressure reservoir conditions will be drawn into a sample accumulator (separator, 103) either as a single oil phase or multiphase fluid (oil phase and water phase). The oil phase can include oil and other hydrocarbons (such as gas that is in solution with oil) and possibly additives or other oil-based fluid (such as oil-based drilling fluid or oil-based treatment fluid) that is soluble in the oil. The water phase can include formation water or brine and possibly additives or other aqueous-based fluid (such as water-based drilling fluid or water-based treatment fluid) that is soluble in the formation water or brine. The separator 103 is configured to separate the oil phase of the reservoir fluid sample from the water phase of the reservoir fluid sample. Pump 2 is configured to transport the oil phase of the reservoir fluid sample into a first analysis chamber 106 that is equipped with one or more sensors or detectors 105 that measure single phase physical and chemical fluid properties, including fluid density and viscosity, of the oil phase at the high temperature and high pressure reservoir conditions. Pump 3 is configured to transport the water phase into a second analysis chamber 110 that is equipped with one or more sensors or detectors 109 that measure single phase physical and chemical fluid properties, including fluid density and viscosity, of the water phase at the reservoir conditions. For example, the sensor(s) 105 and/or the sensor (s) 109 can employ specific sensors and spectroscopic techniques to measure the single phase physical and chemical fluid properties of the distinct oil and water phases. The sensor(s) 105 and/or the sensor(s) 109 can also measure reservoir conditions, including the pressure and temperature of the reservoir fluid under the in-situ reservoir conditions. If the results of the fluid analysis measurements performed by the sensors 105 and 109 show that the collected reservoir fluid is not at desired quality or that the collected reservoir fluid has not been properly separated by separator 103 (e.g., there is a fraction of water phase in the oil phase or vice versa), the reservoir fluid can be loaded from the analysis chambers into one or more waste collection containers (or possibly returned back to the wellbore), an additional fluid sample can be collected from the reservoir formation and separated into oil and water phases by the separator 103, and the fluid analysis measurements can be performed by the sensors 105 and 109 on the additional fluid sample phases. These operations can be performed one or more times until satisfactory results are obtained. Once satisfactory results are obtained, the oil phase and water phase of the reservoir fluid sample can be loaded from the analysis chambers into corresponding collection containers 107 and 111 with the help of pumps 2 and 3.

Data representing the properties measured by the sensors 105 and 109 can be collected and stored in a data store 113 (e.g., electronic memory) and then loaded into a database 115 for processing by the IFT prediction module 117 and the advisory tool 119. The database 115 can be a cloud database as shown. Alternatively, the database 115 can be a local database or other suitable datastore. This database 115 can be linked to the advisory tool 119, which can provide probability of various issues with that sample and potential strategies for production from the well.

The IFT prediction module 117 is configured to determine (or predict or estimate) oil-water IFT of the reservoir fluid sample based on the SSA model of Eqn. (10). Specifically, in block 117A, the critical temperature $T_c$ (or G ($\mu$, $\rho_0$)) of the oil phase of the reservoir fluid sample is determined from the single phase physical and chemical fluid properties, including fluid density and viscosity, of the oil phase of the reservoir fluid sample according to the model of Eqn. (9). In block 117B, the critical temperature $T_c$ (or $G(\mu, \rho_0)$) of the oil phase of the reservoir fluid sample as determined in block 117A as well as the fluid density $\rho_w$ of the water phase of the reservoir fluid sample (measured by the sensors 109) and the fluid density $\rho_o$ of the oil phase of the reservoir fluid sample (measured by the sensors 105) and the temperature T of the formation fluid (measured by the sensor 105 or 109) are input to the SSA model of Eqn. (10) to determine a value of the oil-water IFT of the reservoir fluid sample, which quantifies the IFT between the oil phase and the water phase of the reservoir fluid sample. The database 115 and/or the value of oil-water IFT of the reservoir fluid sample as determined in block 117B can be accessed by (or linked to) the advisory tool 119, which uses the value of oil-water IFT of the reservoir fluid sample as part of operations that provide for analysis and optimization of the formation reservoir. For example, the advisory tool 119 can provide insight into reservoir fluid dynamics as well as various factors that aid scientists and engineers understand the reservoir formation and decide on a production strategy. In one embodiment, the value of the oil-water IFT of the reservoir fluid sample can be used to determine a capillary number for the reservoir formation (for example, using Eqn. (1)) and an estimate of oil reserves for the reservoir formation based thereon (for example, using Eqn. (2)). Such determinations can involve other data calculations, such as capillary pressure and hydrocarbon height in the formation as shown in FIG. 4. Such determinations can be performed while-logging, e.g., while operating the downhole tool as part of the method. In other applications, the advisory tool 119 can use the value of the oil-water IFT of the reservoir fluid sample to simulate or model or optimize oil production or recovery strategies and operations (for example, using Eqn. (3)). The advisory tool 119 can also be configured to use the fluid properties of oil and water phases of the reservoir fluid sample as measured by the downhole fluid analysis to predict corrosive properties of reservoir fluids or predict emulsions in the reservoir fluids and possibly develop treatments that mitigate production issues associated therewith.

In embodiments, the IFT prediction module 117 and/or the advisory tool 119 can be embodied by a computer processing system such as a cloud-based computing environment, server, or other computer system. Alternatively, or additionally, the function of the IFT prediction module 117 and/or the advisory tool 119 can be embodied by an application or container or other distributed software product. In still other embodiments, the functionality of the IFT prediction module 117 can be integrated as part of the advisory tool 119. The data stored in the database 115 can be made accessible to a wide variety of systems and devices, including network computer systems and portable devices such as laptops, tablets and smart phones.

In embodiments, the downhole fluid measurements and the analysis of the IFT prediction module 117 and/or the advisory tool 119 can be performed for multiple zones in a well or multiple wells in a field or in multiple fields in a given formation reservoir to understand potential challenges and develop right strategies for production. In these applications, machine learning based models or analytics-based models can aid in predicting a missing parameter (which is quite common) for a given well or new well or a new zone in a well, based on the historical information contained in the database (e.g., database 115 of FIG. 4 as described herein). The advisory tool 119 can use the machine learning based models or analytics-based models to provide suggestions and solutions for various challenges in a desired reservoir.

In other embodiments, the advisory tool 119 can be smart and configured to self-learn to further improve the SSA model with additional input data. For example, additional laboratory measurements of IFT of reservoir fluids can be fed back to the SSA model for further calibration and fine-tuning.

In still other embodiments, the IFT predicted by the methodology as described herein can be used for quality control of downhole fluid sampling and analysis operations to ensure that the obtained reservoir fluid samples and corresponding analysis measurements are representative of reservoir fluids. For example, if the predicted IFT is too high (such as 100) or too low such as 0 or negative (if possible), then the reservoir fluid samples and corresponding analysis measurements can be determined to be not representative of reservoir fluids. In this case, the fluid densities and/or fluid viscosities of the oil and water phases as measured by the downhole sensors can be determined to be incorrect or not consistent.

It will be appreciated that the methodology as described herein can employ a downhole logging tool (such as a wireline or logging-while-drilling tool) that is conveyable in a wellbore that traverses the reservoir rock under investigation, such as the logging tool described below with respect to FIG. 5.

Figure 5:
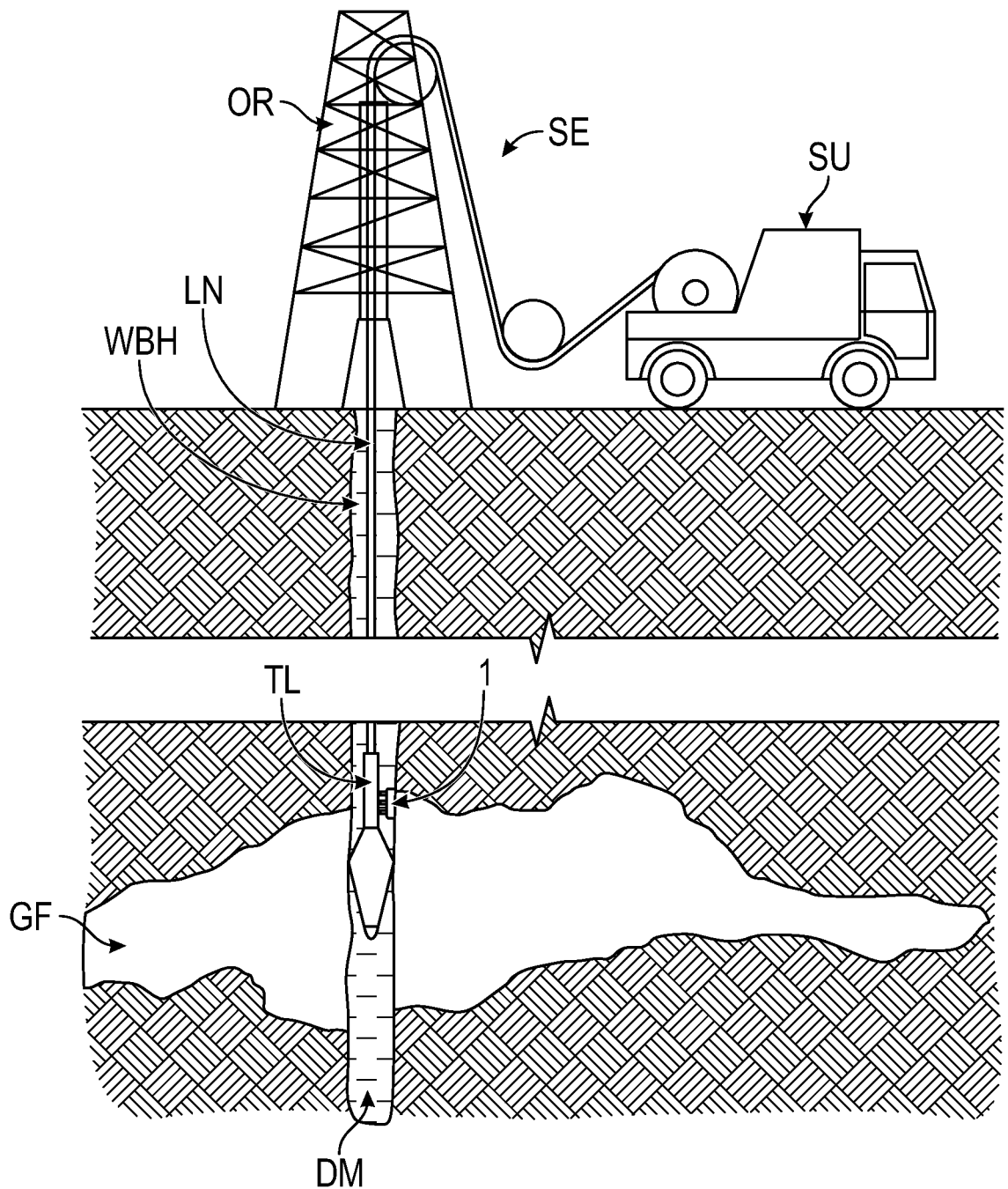
FIG. 5 is a schematic diagram that illustrates an example onshore hydrocarbon well location, which can embody parts of the methodology and systems as described herein.

FIG. 5 is a schematic diagram that illustrates an example onshore hydrocarbon well location with surface equipment SE above a hydrocarbon geological formation GF after drilling operation has been carried out. At this stage, i.e. before a casing string is run and before cementing operations are carried out, the wellbore WBH is filled with a fluid mixture DM, which is typically a mixture of drilling fluid and drilling mud. In this example, the surface equipment SE comprises an oil rig OR and a surface unit SU for deploying a logging tool TL in the wellbore WB. The surface unit may be a vehicle coupled to the logging tool by a wireline cable LN. Further, the surface unit can include an appropriate device for determining the depth position of the logging tool TL relative to the surface level. The logging tool TL can include a centralizer that is configured to insure a correct axial positioning of the logging tool in the wellbore WBH. The logging tool TL includes various tools or sensors for collection and analysis of formation fluids. The logging tool TL can also provide various measurement data related to the analysis of the formation fluids and can possibly be configured to store samples of the formation fluids in containers for transport to the surface and subsequent analysis. The surface unit SU can include appropriate electronic and software arrangements for processing, analyzing and storing the measurement data provided by the logging tool TL. In embodiments, the logging tool TL can be the In-Situ Fluid Analyzer tool that is available from Schlumberger or another suitable logging tool.

It should be appreciated that while FIG. 5 shows a wireline application, the embodiments described herein are equally applicable to logging while drilling applications. That is, there is no need for the logging tool to be limited to an application wherein it is attached to a separate wire or cable controlling its movements, it is possible for the different functionality of the logging tool to be incorporated into the actual drill pipe itself (for example on the drill collar).

Figure 6:
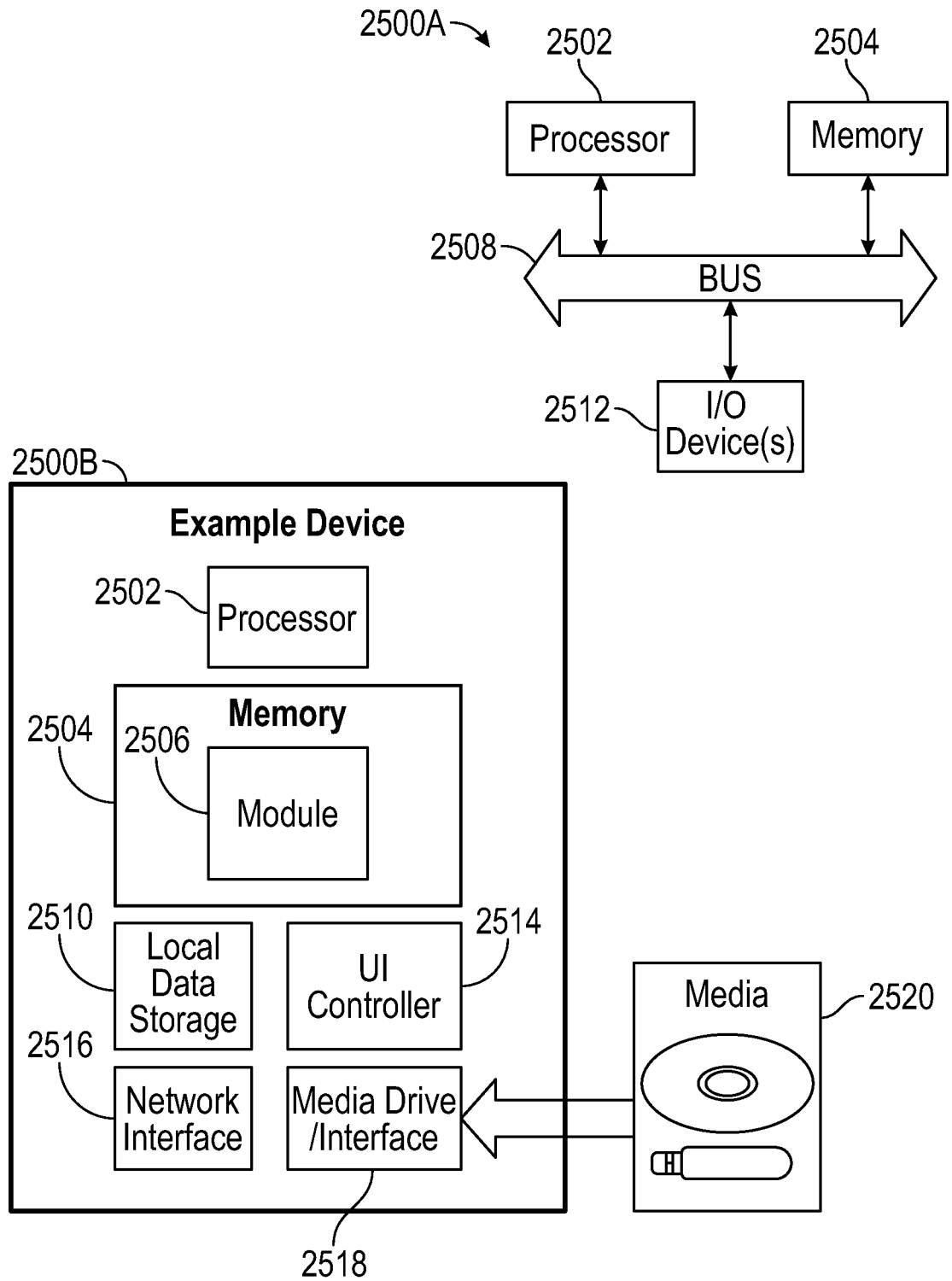
FIG. 6 is a block diagram of a computer processing system, which can be used to embody parts of the methodology and systems as described herein.

FIG. 6 illustrates example devices 2500A, 2500B, each with a processor 2502 and memory 2504 that can be configured to implement various embodiments of the methods and systems described herein, including functionality and operations carried out by the database, IFT prediction module and advisory tool of FIG. 4 as described herein. Memory 2504 can also host one or more databases and can include one or more forms of volatile data storage media such as random-access memory (RAM), and/or one or more forms of nonvolatile storage media (such as read-only memory (ROM), flash memory, and so forth).

Devices 2500A, 2500B illustrated in FIG. 6 are just a few examples of a computing device or programmable device and is not intended to suggest any limitation as to scope of use or functionality of devices 2500A, 2500B and/or their possible architectures. For example, devices 2500A, 2500B can comprise one or more computing devices, programmable logic controllers (PLCs), etc.

Further, devices 2500A, 2500B should not be interpreted as having any dependency relating to one or a combination of components illustrated in devices 2500A, 2500B. For example, devices 2500A, 2500B may include one or more of computers, such as a laptop computer, a desktop computer, a mainframe computer, etc., or any combination or accumulation thereof.

Device 2500A can also include a bus 2508 configured to allow various components and devices, such as processors 2502, memory 2504, and local data storage 2510, among other components, to communicate with each other.

Bus 2508 can include one or more of any of several types of bus structures, including a memory bus or memory controller, a peripheral bus, an accelerated graphics port, and a processor or local bus using any of a variety of bus architectures. Bus 2508 can also include wired and/or wireless buses.

Local data storage 2510 can include fixed media (e.g., RAM, ROM, a fixed hard drive, etc.) as well as removable media (e.g., a flash memory drive, a removable hard drive, optical disks, magnetic disks, and so forth).

One or more input/output (I/O) device(s) 2512 may also communicate via a user interface (UI) controller 2514, which may connect with I/O device(s) 2512 either directly or through bus 2508.

In one possible implementation, a network interface 2516 may communicate outside of device 2500B via a connected network.

A media drive/interface 2518 can accept removable tangible media 2520, such as flash drives, optical disks, removable hard drives, software products, etc. In one possible implementation, logic, computing instructions, and/or software programs comprising elements of module 2506 may reside on removable media 2520 readable by media drive/interface 2518. Various processes of the present disclosure or parts thereof can be implemented by instructions and/or software programs that are elements of module 2506. Such instructions and/or software programs may reside on removable media 2520 readable by media drive/interface 2518 as is well known in the computing arts.

In one possible embodiment, input/output device(s) 2512 can allow a user (such as a human annotator) to enter commands and information to device 2500A and allow information to be presented to the user and/or other components or devices. Examples of input device(s) 2512 include, for example, sensors, a keyboard, a cursor control device (e.g., a mouse), a microphone, a scanner, and any other input devices known in the art. Examples of output devices include a display device (e.g., a monitor or projector), speakers, a printer, a network card, and so on.

Various processes or parts of the method or workflow of the present disclosure may be described herein in the general context of software or program modules, or the techniques and modules may be implemented in pure computing hardware. Software generally includes routines, programs, objects, components, data structures, and so forth that perform particular tasks or implement particular abstract data types. An implementation of these modules and techniques may be stored on or transmitted across some form of tangible computer-readable media. Computer-readable media can be any available data storage medium or media that is tangible and can be accessed by a computing device. Computer readable media may thus comprise computer storage media. "Computer storage media" designates tangible media, and includes volatile and non-volatile, removable and non-removable tangible media implemented for storage of information such as computer readable instructions, data structures, program modules, or other data. Computer storage media include, but are not limited to, RAM, ROM, EEPROM, flash memory or other memory technology, CD-ROM, DVD or other optical storage, magnetic cassettes, magnetic tape, magnetic disk storage or other magnetic storage devices, or any other tangible medium which can be used to store the desired information, and which can be accessed by a computer.

In embodiments, any one or any portion or all of the steps or operations of the method or workflow as described above can be performed by a processor. The term "processor" should not be construed to limit the embodiments disclosed herein to any particular device type or system. The processor may include a computer system. The computer system may also include a computer processor (e.g., a microprocessor, microcontroller, digital signal processor, or general-purpose computer) for executing any of the methods and processes described above.

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Some of the methods and processes described above, can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively, or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method for characterizing interfacial tension (IFT) of reservoir fluids, comprising:
   a) obtaining fluid property data that represents fluid properties of a reservoir fluid sample measured downhole at reservoir conditions by a downhole tool;
   b) performing, using the downhole tool, downhole measurements of the fluid properties of the reservoir fluid sample by inputting the fluid property data to a computational model that determines a value of oil-water IFT of the reservoir fluid sample based on the fluid property data; and
   c) predicting, using the downhole tool, emulsions in reservoir fluids and developing treatments that mitigate production issues associated therewith based on the fluid property data measured downhole at the reservoir conditions.

2. The method according to claim 1, wherein:
the operations of a) through c) are performed by a processor.

3. The method according to claim 2, wherein:
the processor is part of a cloud-based computing environment.

4. The method according to claim 1, further comprising:
storing the value of the oil-water IFT of the reservoir fluid sample as part of data accessible by an advisory tool for reservoir analysis and optimization.

5. The method according to claim 4, wherein:
the advisory tool is provided by a cloud-based computing environment for reservoir analysis and optimization.

6. The method according to claim 1, wherein:
the fluid property data represents single-phase fluid properties of the reservoir fluid sample.

7. The method according to claim 6, wherein:
the single-phase fluid properties of the reservoir fluid sample comprise fluid density and viscosity of an oil phase of the reservoir fluid sample.

8. The method according to claim 6, wherein:
the single-phase fluid properties of the reservoir fluid sample further comprises a fluid density of a water phase of the reservoir fluid sample.

9. The method according to claim 1, wherein:
the computational model relates critical temperature of an oil phase of the reservoir fluid sample to the value of the oil-water IFT of the reservoir fluid sample.

10. The method according to claim 9, wherein:
the computation model relates single-phase fluid properties of the oil phase of the reservoir fluid sample to the critical temperature of the oil phase of the reservoir fluid sample.

11. The method according to claim 10, wherein:
the single-phase fluid properties of the oil phase of the reservoir fluid sample comprise a fluid density and a viscosity of the oil phase of the reservoir fluid sample.

12. The method according to claim 1, wherein:
the computational model has the form $$\gamma_{OW} = \left[\frac{1.58(\rho_w - \rho_o) + 1.76}{\left(\frac{T}{G(\mu, \rho_0)}\right)^{0.3125}}\right]^4,$$

where $\gamma_{OW}$, is the value of the oil-water IFT of the reservoir fluid sample, $\rho_w$ and $\rho_o$ are density of a water phase and oil phase, respectively, T is the reservoir fluid temperature as part of the reservoir conditions, and $G(\mu, \rho_0)$ represents a critical temperature of the oil phase given the fluid density $\rho_0$ and viscosity $\mu$ of the oil phase.

13. The method according to claim 1, further comprising:
storing the value of the oil-water IFT of the reservoir fluid sample in a cloud-based database or a local database.

14. The method according to claim 1, wherein:
the downhole measurements are configured to measure single-phase fluid properties of the reservoir fluid sample.

15. The method according to claim 14, wherein:
the single-phase fluid properties of the reservoir fluid sample comprise a fluid density and a viscosity of an oil phase of the reservoir fluid sample.

16. The method according to claim 14, wherein:
the single-phase fluid properties of the reservoir fluid sample further comprise a fluid density of a water phase of the reservoir fluid sample.

17. The method according to claim 1, wherein:
the operations are performed for multiple zones in a well or multiple wells in a field or multiple fields in a given formation reservoir.

18. A system for reservoir analysis, comprising:
at least one processor configured to:
   a) obtain fluid property data that represents fluid properties of a reservoir fluid sample measured downhole at reservoir conditions by a downhole tool;
   b) perform, using the downhole tool, downhole measurements of the fluid properties of the reservoir fluid sample by inputting the fluid property data to a computational model that determines a value of oil-water IFT of the reservoir fluid sample based on the fluid property data; and
   c) predict, using the downhole tool, emulsions in reservoir fluids and developing treatments that mitigate production issues associated therewith based on the fluid property data measured downhole at the reservoir conditions.

19. The system according to claim 18, wherein:
the system interfaces to or is part of an advisory tool.

20. The system according to claim 19, wherein:
the advisory tool is configured to use the value of the oil-water IFT of the reservoir fluid sample to determine a capillary number for a reservoir formation and an estimate of oil reserves for the reservoir formation.

21. The system according to claim 19, wherein:
the advisory tool is configured to use the value of the oil-water IFT of the reservoir fluid sample to simulate or model or optimize oil production or recovery strategies.

22. The system according to claim 19, wherein:
the advisory tool is configured to use the fluid property data measured downhole at reservoir conditions to predict corrosive properties of reservoir fluid and to develop treatments that mitigate production issues associated therewith.

23. The system according to claim 18, wherein:
the at least one processor is part of a cloud-based computing environment.

24. The system according to claim 18, wherein:
the at least one processor is further configured to store the value of the oil-water IFT of the reservoir fluid sample in a database.

25. The system according to claim 18, wherein:
the fluid property data represents single-phase fluid properties of the reservoir fluid sample.

26. The system according to claim 18, wherein:
the computational model relates critical temperature of an oil phase of the reservoir fluid sample to the value of the oil-water interfacial tension of the reservoir fluid sample.

* * * * *